United States Patent [19]

Zimmerman et al.

[11] Patent Number: 5,166,158
[45] Date of Patent: Nov. 24, 1992

[54] METHOD FOR THE TREATMENT OF APNEA AND/OR BRADYCARDIA

[75] Inventors: Andrew W. Zimmerman; Christopher A. Miller; Mark S. Gaylord; Vichien Lorch, all of Knoxville, Tenn.

[73] Assignee: The University of Tennessee Research Corporation, Knoxville, Tenn.

[21] Appl. No.: 632,048

[22] Filed: Dec. 20, 1990

[51] Int. Cl.$^5$ ............................................ A61K 31/505
[52] U.S. Cl. ............................................ 514/269
[58] Field of Search ........................................ 514/269

[56] References Cited

PUBLICATIONS

Daley, R. D., Anal. Prof. Drug Subst., 2: 409-37 (1973) (Chemical Abstracts 79 (8) 45858h).
Kjellin et al., 1982, Chem. Abs. 96 (17): 142881u. 3,8--Dialkylxanthines compositon and methods for the treatment of chronic obstructive airway disease & cardiovascular diseases.
Hamilton 1987, Chem. Abs. 107 (7) 59053a. Pyrazolo[4,3-d]pyrimidine-5,7-[4H,6H]dione or -5-thione-7-one analogs.
Singh et al., 1986, Chem. Abs. 105 (23): Synthesis of novel pyrimidine diones and thiazolidinones as cardiovascular agents.

Primary Examiner—Frederick E. Waddell
Assistant Examiner—Diane Gardner
Attorney, Agent, or Firm—Luedeka, Hodges, Neely & Graham

[57] ABSTRACT

Treatment of apnea and/or bradycardia employing 5-ethyldihrdo-5-phenyl-4,6-[1H,5H]-pyrimidenedione (primidone).

4 Claims, No Drawings

METHOD FOR THE TREATMENT OF APNEA AND/OR BRADYCARDIA

This invention relates to the treatment of apnea and/or bradycardia, particularly in infants.

Apnea, defined as the cessation of the breathing function for a time period of at least 20 seconds, is a problem affecting 50–75% of infants born prior to 33 weeks of gestation. Apnea frequently is accompanied by bradycardia, defined as a heart beat rate of less than 200 beats per minute and frequently including blood oxygen desaturation. Infants with severe apnea of prematurity are predisposed to increased incidences of cerebral palsy, developmental delay and retinopathy of prematurity. Apnea in adults is also observed, but with less frequency.

In the prior art, treatment of apnea has traditionally included methyl xanthine medications, (e.g., theophylline or caffeine) after identifiable causes (infection, anemia, hypoxia, atelectasis or intraventricular hemorrhage) have been corrected. In a substantial number of instances (up to about 37%), the apnea has been found to be refractory to theophylline or caffeine and/or treatment by such prior art techniques otherwise is not sufficiently effective. In such instances intervention with mechanical ventilation may be indicated. The actual physical event of mechanical ventilation and its duration are traumatic in nature and frequently are associated with complications such as sepsis, ventilation, lung disease, bronchopulmonary dysplasia, and additional hospital days.

Apnea in very premature infants is of particular concern in view of the frequency of its occurrence among this population. Obviously, mechanical ventilation, aside from its traumatic and other potentially adverse effects upon the infant, is economically burdensome. Treatment of such infants for underlying causes of apnea or other medical problems is complicated when the infant is involved in mechanical ventilation.

Accordingly, it is an object of the present invention to provide a method for the treatment of apnea and/or bradycardia.

It is another object to provide a method for reducing the frequency of apnea and or bradycardia events in a mammal.

It is another object to provide a medicament which is effective in reducing or eliminating the requirement for mechanical ventilation intervention as a treatment for apnea and/or bradycardia.

In accordance with the present invention, it has been found that the administration to a mammal suffering from, or which is a suspected candidate for, apnea and/or bradycardia, of an effective amount of 5-ethyldihydro-5-phenyl-4-6[1H,5H]-pyrimidinedione, i.e., primidone, in a physiologically acceptable, non-toxic vehicle will effectively reduce or eliminate apnea and/or bradycardia events, whether or not such events are accompanied by bradycardia events. In one embodiment of the method of the present invention, there is administered to the mammal a quantity of between about 10 mg and about 15 mg of the medicament primidone in saline solution per kg of body weight per day. In infants, the preferred routes of administration are orally or nasogastrically. Surprisingly, it has been also found that such medicament is effective in reducing and/or eliminating the need for mechanical ventilation intervention of such mammals, thereby reducing or eliminating the adverse effects that are frequently associated with such mechanical intervention.

Whereas the etiologies of apnea and/or bradycardia are unknown with certainty, the present inventors hypothesize that apnea and/or bradycardia may be associated with "immaturity" of brainstem pathways, possibly based upon delayed myelination as well as membrane phosphorylation. It is also postulated that there may be a possible association between respiratory regulation and hemorrhage due to the deposition of protein and/or peptides from serum in the brainstem, or deposition of iron salts and/or peroxidative damage following lysis of red cells. In any event, without being bound to any specific etiology, the present inventors have found that the administration of primidone is effective in reducing the frequency of events of apnea and/or bradycardia, particularly in infants of less than about 50 days age. It is further believed that such medicament is especially effective in the treatment of apnea in infants born after less than about 33 weeks of gestation.

Experimentally, the present inventors selected sixteen infants, all of which were known sufferers of apnea and bradycardia. For the initial investigation, only infants which appeared refractory to theophylline were chosen. No effort was made to select infants by presumed pathogenesis, by associated clinical findings or by outcome. The gestational ages of the infants and the number of days following birth at which the present treatment was initiated are given in Table I.

TABLE I

| Patient No. | Gestational Age (weeks) | Day of Initiation of Treatment (after birth) |
|---|---|---|
| 1 | 32 | 35 |
| 2 | 32 | — |
| 3 | 27 | 43 |
| 4 | 27 | 41 |
| 5 | 25 | 47 |
| 6 | 26 | 30 |
| 7 | 25 | 27 |
| 8 | 29 | 15 |
| 9 | 30 | 35 |
| 10 | 29 | 27 |
| 11 | 27 | 33 |
| 12 | 25 | 55 |
| 13 | 28 | 39 |
| 14 | 28 | 57 |
| 15 | 28 | 28 |
| 16 | 28 | 13 |

The presence or absence of intraventricular hemorrhage and EEG findings relating to the infants were examined. EEGs were available for 14 of the infants and were normal for corrected gestational age in 10 of the 14, and mildly abnormal for four infants, due to "increased slowing for age". No epileptiform abnormalities were noted. Cranial sonograms were available for 14 of the 16 infants and were normal in nine infants. Three infants had evidence for grade I or II hemorrhage (Papile criteria) and two infants had evidence of grade III IVH. Some infants had experienced mechanical ventilation.

Theophylline treatment had been instituted early in each infant's course (mean=5.2 days or life +/−3 days). In thirteen infants, theophylline treatment had begun while the infants were undergoing assisted ventilation. While many of the infants were experiencing bradycardia events, theophylline treatment had begun in several in order to assist the infant in weaning from the ventilator. Ten of the sixteen infants had been successfully weaned from the ventilator but were experiencing persistence or reoccurrence of apnea and/or bradycardia despite adequate theophylline levels. The remaining six infants were experiencing ongoing bradycardia, with or without associated apnea, despite therapeutic theophylline levels and assisted ventilation. All infants had theophylline levels at the time of the initiation of the present therapy, ranging from 6.0 µg/ml to 12.7 µg/ml with a mean of 9.3 µg/ml.

The number of apneic and bradycardia events exhibited by each infant was recorded for the 24 hour interval prior to treatment with primidone. Primidone treatment was initiated at a mean age of 35 days of life (+/−12.6 days). Each infant was administered between about 10 and 15 mg/kg of body weight of primidone daily. Treatment was continued for at least 3 days and was terminated thereafter when deemed medically appropriate. Administration was either orally or nasogastrically as was most convenient for each infant. Equal aliquots of the daily dosage was administered at regular intervals of 8 hours. No complications were associated with the use of the medication, even in infants which were still undergoing assisted ventilation.

The usual clinical parameters for a population of this nature appeared typical during the course of the study. Hematocrits varied over the course of the hospitalization, ranging from between 34.6 and 57% during the period between the initiation of theophylline therapy and initiation of the primidone therapy. Glucose and calcium levels were within the normal range.

The frequency of apneic events and bradycardia events in the 16 infants were recorded at time intervals of 24, 48 and 72 hours following initiation of the primidone therapy. Frequency of apneic and bradycardia events for each infant before initiation of the primidone therapy are listed in TABLE II and the frequency of such events after treatment are listed in TABLE III.

TABLE II

| Patient | Prior to Primidone Therapy | |
|---|---|---|
| | Apneic Events 24 hr | Bradycardia Events 24 hr |
| 1 | 6 | 6 |
| 2 | 12 | 21 |
| 3 | 24 | 24 |
| 4 | 12 | 20 |
| 5 | 8 | 10 |
| 6 | 0 | 0 |
| 7 | 0 | 0 |
| 8 | 13 | 17 |
| 9 | 2 | 2 |
| 10 | 3 | 12 |
| 11 | 2 | 2 |
| 12 | 11 | 5 |
| 13 | 27 | 22 |
| 14 | 10 | 10 |
| 15 | 8 | 10 |
| 16 | 1 | 1 |

TABLE III

| | After Primidone Therapy | | | | | |
|---|---|---|---|---|---|---|
| | Apneic Events | | | Bradycardia Events | | |
| Patient | 24 hr | 48 hr | 72 hr | 24 hr | 48 hr | 72 hr |
| 1 | 2 | 0 | 5 | 2 | 0 | 5 |
| 2 | 3 | 3 | 5 | 3 | 6 | 9 |
| 3 | 10 | 10 | 12 | 13 | 10 | 12 |
| 4 | 2 | 2 | 5 | 2 | 4 | 8 |
| 5 | 1 | 0 | 5 | 1 | 1 | 5 |
| 6 | 8 | 1 | 3 | 6 | 2 | 4 |
| 7 | 2 | 1 | 0 | 2 | 1 | 0 |
| 8 | 7 | 8 | 9 | 7 | 9 | 9 |
| 9 | 2 | 0 | 1 | 2 | 0 | 1 |
| 10 | 0 | 1 | 0 | 0 | 1 | 0 |
| 11 | 0 | 0 | 0 | 0 | 0 | 0 |
| 12 | 3 | 4 | 3 | 2 | 3 | 4 |
| 13 | 0 | 0 | 0 | 0 | 0 | 0 |
| 14 | 5 | 2 | 0 | 5 | 4 | 0 |
| 15 | 0 | 1 | 0 | 0 | 3 | 0 |
| 16 | 1 | 4 | 0 | 2 | 4 | 0 |

As shown in TABLES II and III, apneic events decreased significantly when the number of events in the 24 hours prior to initiation of the primidone treatment were compared with the number of events 24, 48, and 72 hours subsequent to treatment. Mean apneic events in the 24 hours interval prior to primidone treatment were 8.6; values following primidone treatment (mean) were 3.0 for the first day after treatment (p=0.008), 3.5 for the second day following treatment (p=0.002), and 3.2 for the third day following treatment (p=0.005).

Bradycardia events deceased even more significantly with primidone treatment, from a mean of 10.1 events in the 24 hours prior to primidone treatment, to values of 3.6 events for the first day following primidone treatment, 3.99 for the second day and 3.95 for the third day following treatment (p=0.001).

The present inventors found no evidence, clinically or from EEG studies, in the infants treated as disclosed herein, of convulsive activity associated with the infants' apnea or bradycardia.

None of the infants treated as above required assisted ventilation following initiation of the primidone treatment, aside from the six which were undergoing assisted ventilation at the inception of primidone treatment. Due to their improved medical condition as a result of the primidone treatment, each of the infants was released from hospital care earlier than normally expected for infants exhibiting like events of apnea and/or bradycardia and which had not been treated with primidone. These factors are indicative of an economic advantage in addition to the medical advantage of the present invention.

Whereas the present treatment was conducted with infants, it is believed that primidone will be useful in the treatment of adult apnea. Its use in lieu of theophylline, caffeine or similar traditional treatments is also indicated.

What is claimed is:

1. A method for the treatment of apnea or bradycardia in mammals comprising the administration to said mammal of a pharmaceutically effective amount of 5-ethyldihydro-5-phenyl-4,6[1H,5H]-pyrimidinedione in a physiologically acceptable, non-toxic, vehicle.

2. The method of claim 1 wherein said mammal is of an age of between birth and about 50 days.

3. The method of claim 1 wherein said effective amount of 5-ethyldihydro-5-phenyl-4,6[1H,5H]-pyrimidinedione is between about 10 and about 15 mg/kg of body weight/day.

4. A method for the reduction of apneic and/or bradycardia events in a mammal comprising the administration to said mammal of a pharmaceutically effective amount of 5-ethyldihydro-5-phenyl-4,6[1H,5H]-pyrimidinedione in a physiologically acceptable, non-toxic, vehicle.

* * * * *